(12) United States Patent
Gong et al.

(10) Patent No.: US 10,888,411 B2
(45) Date of Patent: Jan. 12, 2021

(54) INTRAVASCULAR STENT AND MANUFACTURING METHOD THEREOF

(71) Applicant: SUZHOU INNOMED MEDICAL DEVICE CO., LTD., Jiangsu (CN)

(72) Inventors: Xiaoyan Gong, Jiangsu (CN); Weikun Zhou, Jiangsu (CN); Qianqian Zhang, Jiangsu (CN)

(73) Assignee: SUZHOU INNOMED MEDICAL DEVICE CO., LTD., Jiangsu (CN)

( * ) Notice: Subject to any disclaimer, the term of this patent is extended or adjusted under 35 U.S.C. 154(b) by 321 days.

(21) Appl. No.: 15/571,737

(22) PCT Filed: May 4, 2016

(86) PCT No.: PCT/CN2016/080962
§ 371 (c)(1),
(2) Date: Feb. 28, 2018

(87) PCT Pub. No.: WO2016/177323
PCT Pub. Date: Nov. 10, 2016

(65) Prior Publication Data
US 2018/0153676 A1 Jun. 7, 2018

(30) Foreign Application Priority Data

May 4, 2015 (CN) .......................... 2015 1 0219825
May 4, 2015 (CN) ..................... 2015 2 0278034 U
(Continued)

(51) Int. Cl.
*A61F 2/06* (2013.01)
*A61F 2/90* (2013.01)
(Continued)

(52) U.S. Cl.
CPC .................. *A61F 2/06* (2013.01); *A61F 2/90* (2013.01); *A61F 2/91* (2013.01);
(Continued)

(58) Field of Classification Search
CPC ...... A61F 2/06; A61F 2/90; A61F 2/91; A61F 2/88; A61F 2230/0069; A61F 2250/0098; A61F 2220/0058; A61F 2230/0017
See application file for complete search history.

(56) References Cited

U.S. PATENT DOCUMENTS 5,007,926 A * 4/1991 Derbyshire ............... A61F 2/92
606/191
5,922,020 A * 7/1999 Klein ........................ A61F 2/91
606/194

(Continued)

FOREIGN PATENT DOCUMENTS

CN 201150578 Y 11/2008
CN 103271785 A 9/2013
(Continued)

OTHER PUBLICATIONS

International Search Report and Written Opinion for International Application No. PCT/CN2016/080962 dated Jul. 28, 2016.
(Continued)

*Primary Examiner* — Paul B Prebilic
(74) *Attorney, Agent, or Firm* — K&L Gates LLP; Louis C. Cullman; Georgia N. Kefallinos (57) ABSTRACT

Disclosed herein is an intravascular stent for being implanted into blood vessels and a method for manufacturing the same. The intravascular stent is woven by at least one weaving wire, and the stent is in a tubular structure. The at least one wire has an even number of free ends, and the free ends of the at least one wire are aligned and jointed together with each other, which have cutting portions. The cutting
(Continued)

portions of the two free ends that are aligned and jointed with each other match each other to make the two free ends be engaged into a joint portion with a diameter identical to that of the wire. The intravascular stent has seamless connection, and the distribution of radial force and axial force of the free ends is uniform, leading to convenience for laser welding. Moreover, the intravascular stent has great flexibility, excellent operability and perfect appearance.

19 Claims, 6 Drawing Sheets

(30) Foreign Application Priority Data

May 4, 2015 (CN) .................... 2015 2 0278783 U
May 4, 2015 (CN) .................... 2015 2 0278784 U (51) Int. Cl.
*A61F 2/91* (2013.01)
*A61F 2/82* (2013.01)

(52) U.S. Cl.
CPC . *A61F 2002/828* (2013.01); *A61F 2230/0067* (2013.01); *A61F 2240/001* (2013.01); *A61F 2250/0098* (2013.01)

(56) References Cited

U.S. PATENT DOCUMENTS

| | | | | |
|---|---|---|---|---|
| 6,048,360 A * | 4/2000 | Khosravi | ................. | A61F 2/92 600/36 |
| 6,083,257 A * | 7/2000 | Taylor | ................. | A61F 2/90 623/1.46 |
| 6,221,100 B1 | 4/2001 | Strecker | | |
| 6,248,190 B1 * | 6/2001 | Stinson | ................. | A61F 2/90 148/519 |
| 7,462,192 B2 * | 12/2008 | Norton | ................. | A61F 2/90 264/103 |
| 8,409,270 B2 * | 4/2013 | Clerc | ................. | A61F 2/90 623/1.15 |
| 2003/0028245 A1 * | 2/2003 | Barclay | ................. | A61F 2/88 623/1.22 |
| 2004/0106985 A1 * | 6/2004 | Jang | ................. | A61F 2/91 623/1.16 |
| 2004/0116831 A1 * | 6/2004 | Vrba | ................. | A61F 2/013 600/585 |
| 2004/0167441 A1 | 8/2004 | Reynolds et al. | | |
| 2006/0064156 A1 * | 3/2006 | Thistle | ................. | A61F 2/90 623/1.16 |
| 2007/0112415 A1 * | 5/2007 | Bartlett | ................. | A61F 2/90 623/1.15 |
| 2008/0290076 A1 * | 11/2008 | Sheldon | ................. | A61F 2/90 219/121.64 |

FOREIGN PATENT DOCUMENTS

| | | |
|---|---|---|
| CN | 103356315 A | 10/2013 |
| CN | 103767810 A | 5/2014 |
| CN | 104799983 A | 7/2015 |
| CN | 204671330 U | 9/2015 |
| CN | 204766039 U | 11/2015 |
| CN | 204766052 U | 11/2015 |
| WO | 2005/067816 A1 | 7/2005 |
| WO | 2008/051935 A1 | 5/2008 |
| WO | 2016/177323 A1 | 11/2016 |

OTHER PUBLICATIONS

Supplementary Partial European Search Report for European Patent Application No. 16789317 dated Dec. 10, 2018.

* cited by examiner

INTRAVASCULAR STENT AND MANUFACTURING METHOD THEREOF

CROSS REFERENCE TO RELATED APPLICATIONS

This application claims the benefit of, and priority to, Chinese Patent Application Serial Nos. 201510219825.7, 201520278784.4, 201520278034.7, and 201520278783.X, filed on May 4, 2015, the entire disclosures of which are hereby incorporated by reference in their entireties.

FIELD OF THE INVENTION

Generally, the present disclosure relates to medical devices for minimal invasive surgery. In particular, the present disclosure relates to intravascular stents to be implanted into vessels and methods for manufacturing the same.

BACKGROUND OF THE INVENTION

Peripheral vascular surgery is a traditional method for treating peripheral vascular stenosis. Compared to the traditional peripheral vascular surgery, stent therapy is a minimal invasive surgery with small trauma, reduced complications, improved efficiency due to utilization of stent, Thus, nowadays, stent therapy becomes a main way to treat peripheral vascular stenosis.

In the prior arts, stents are made by weaving wires with free ends. However, the prior arts do not define how the free ends of the wires connect with each other. Traditionally, the free ends are connected with each other by jointing two free ends of the wires side by side to form a stacking portion, covering the stacking portion by a tube with the two free ends exposed out of the tube and then removing the exposed portion.

The traditional stents have shortcomings that: a gap exists between the jointed free ends and thus the blood will penetrate through the gap to affect the service life of the stent; the increased diameter of the connection portion of the stent results in uneven distribution of radial force and axial force of the free ends; and the poor flexibility of the stent has influence on the appearance of the stent.

Meanwhile, the radiopaque performance of intravascular stent in X-ray machines or other medical imaging equipment plays a vital role in clinical effects during surgery and after surgery. During the surgery, the operator needs to accurately position and release the stent by virtue of the radiopaque performance of intravascular stent. The traditional stents need to use a radiopaque ring or mark. However, the radiopaque ring or mark is easy to fall off, which results in high processing requirements, and the addition of mark will make the topical diameter of the stent become larger, which affects the stress distribution and softness of the stent. Moreover, the costs for radiopaque weaving wires are very high, and thus stents woven by radiopaque weaving wires overall will cause high price and waste precious metal.

In addition, the inner wall of the blood vessel is an irregular inner wall with non-uniform diameter. Normally, the diameter is gradually increased and decreased.

In the prior arts, the intravascular stents are cylindrical, which will cause topical compression to the inner wall of blood vessel or topical insufficient support when being implanted into vessels.

SUMMARY OF THE INVENTION

In view of the problems existing in the prior arts, intravascular stents to be implanted into blood vessels and methods for manufacturing the same are provided herein.

In one aspect, an intravascular stent which is used for being implanted into blood vessels is provided herein. The intravascular stent is woven by at least one wire and is in a tubular structure. The at least one wire have an even number of free ends. The free ends of the at least one wire are aligned and jointed together with each other, each of which has a cutting portion. The said cutting portions of the two free ends match each other to make the two free ends be engaged into a joint portion with a diameter identical to that of the wire.

In one embodiment, the joint portion is covered by a coupling tube, and the inner wall of the coupling tube is seamlessly connected to the outer wall of the joint portion.

In one embodiment, the cutting portion of the free end is a semi-cylinder. The cutting portion includes a top end surface, a bottom end surface and a side wall surface. The two side wall surfaces of the two cutting portions that are aligned and jointed together are abutted against each other, and the two top end surfaces are respectively abutted against the corresponding bottom end surfaces. For example, the two side wall surfaces have a matching concave-convex structure.

In one embodiment, the cutting portion of the free end has a concave-convex structure.

In one embodiment, the coupling tube is a C-Clip tube.

In one embodiment, the cutting portions of the two free ends that are aligned and jointed together are fixed by laser welding.

In one embodiment, the coupling tube and the joint portion are fixed by laser welding or clamping deformation.

In one embodiment, the intravascular stent is woven by forward braiding and backward braiding the at least one wire in a crossing-overlapping mode. The forward braiding wire and backward braiding wire peripherally adjacent to each other form diamond grid units. The switching section of the forward braiding wire and backward braiding wire are rounded corners at the two ends of the stent. The obtuse angles ∅ of the diamond grid units range from 91 to 179 degrees, or from 100 to 160 degrees, or from 110 to 150 degrees, or from 115 to 140 degrees, or from 120 to 135 degrees. The shape of the cross section of the wires is round, ellipse, trapezoid, diamond, or rectangle. The wire is made from any of the following materials: nickel-titanium alloy, 304 stainless steel, 316L stainless steel, L605 cobalt-chromium alloy, and MP35N alloy.

In another aspect, a method for manufacturing the intravascular stent is provided herein. The method comprises the following steps: forward braiding and backward braiding at least one wire in a crossing-overlapping mode with exposed free ends of the wire; cutting the exposed free ends to form cutting portions; connecting the cutting portions of the two free ends which are aligned and jointed together.

In one embodiment, forward braiding and backward braiding at least one wire in a crossing-overlapping mode comprises: forward braiding the at least one wire from the front to the back, and backward braiding the wire from the back to the front when the wire is braided to the tail. The forward braiding wire and the backward braiding wire peripherally adjacent to each other is in a crossing-overlapping mode and forms diamond grid units. The stent is in a tubular structure.

In one embodiment, the method further includes: connecting the two free ends that are aligned and jointed together with a coupling tube and fixing the coupling tube to the free ends. For example, fixing the coupling tube to the free ends includes: performing laser welding to seamlessly weld the coupling tube and the free ends as a whole; or clamping the coupling tube to make the coupling tube and the free ends be seamlessly fixed as a whole; or clamping the coupling tube and then performing laser welding to seamlessly weld the coupling tube and the free ends as a whole.

In yet another aspect, an intravascular stent which is used for being implanted into blood vessels is provided herein. The intravascular stent is woven by at least two wires and the stent is in a tubular structure. The at least two wires have an even number of free ends. The free ends of the at least two wires are aligned and jointed together with each other, and are sleeved by coupling tubes. At least part of the coupling tubes is radiopaque coupling tube and/or at least one of the wires are radiopaque wire.

In one embodiment, the stent is woven by eight wires, in which any one of the wires is a radiopaque wire.

In one embodiment, the radiopaque wire includes a core formed by radiopaque material and an outer peripheral portion wrapped around the core. The cross-sectional area of the core comprises of 30%-50% of the cross-sectional area of the wire. The outer peripheral portion is made of nickel-titanium alloy. Alternatively, the radiopaque wire may be made by mixing radiopaque material and nickel-titanium alloy. The radiopaque material is 10-90% of the nickel-titanium by mass. The radiopaque material is selected from any of the following materials: platinum, platinum iridium alloy, tantalum, gold and the like.

For example, the cross-sectional shape of the radiopaque coupling tube is circular, hexagonal or C-shaped.

In one embodiment, the radiopaque coupling tube(s) is set at one or both ends of the stent or is distributed evenly along the axial direction of the stent.

In one embodiment, the tubular structure of the stent has two ends, one of which is a narrow end and the other is a wide end. The stent is in a tapered cylinder structure with the diameter gradually increased from the narrow end to the wide end.

In still another aspect, an intravascular stent which is used for being implanted into blood vessels is provided herein. The intravascular stent is woven by at least two wires and the stent is in a tubular structure. The at least two wires have an even number of free ends. The free ends of the at least two wires are aligned and jointed together with each other. The tubular structure of the stent has two ends, one of which is a narrow end and the other is a wide end. The diameter of the narrow end is smaller than the diameter of the wide end. The stent is in a tapered cylinder structure with the diameter gradually increased from the narrow end to the wide end.

In one embodiment, the length of the intravascular stent is larger than 100 mm, and the diameter ratio of the wide end and the narrow end ranges from 1.1 to 1.5.

In one embodiment, at least one of the wires is a radiopaque wire.

In one embodiment, the free ends that are aligned and jointed together are covered by coupling tubes, and at least part of the coupling tubes are radiopaque coupling tube.

The beneficial effects achieved by the intravascular stent as described herein are as follows:

1. The joint portion of the free ends of the wire is seamlessly connected to the coupling tube to prevent the blood from penetrating into the gap between the jointed free ends and affecting the service life of the stent. Such configuration can effectively increase the service life of the stent.
2. Each free end of the wire has a cutting portion, such that the diameter of the joint portion formed by the free ends that are aligned and jointed together is identical to the diameter of the wire. The diameter of the joint portion is reduced, and thus the radial force and axial force of the free ends are distributed uniformly.
3. Presence of the cutting portion of each free end results in increased contact area between the free ends. As such, it is convenient for laser welding of the free ends.
4. The stent is excellent in softness, operability and appearance.
5. The stent in a tapered cylinder structure matches the inner wall of the blood vessel. Such stent provides uniform pressure to the inner wall of blood vessels and will not cause topical compression or topical insufficient support within the vessels.
6. The radiopaque performance of the stent is excellent, and the radiopaque cost of the stent is reduced, and meanwhile the stress distribution of the stent is not affected.

In the drawings, 1—woven wire, 2/2'/2"—free end, 3—cutting portion, 31—top end surface, 32—bottom end surface, 33—side wall surface, 4—joint portion, 5/5'—coupling tube, 6—radiopaque wire, 61—core, 62—outer peripheral portion, 7—narrow end, 8—wide end.

DETAILED DESCRIPTION OF THE INVENTION

The present invention is described as below in details by reference to appended drawings, to make the object, technical solution and advantages of the present invention more apparent. It is noted that the invention is not limited to the construction shown in the drawings, and various combinations of the various embodiments of the invention may be made without departing from the spirit of the invention.

Hereinafter, specific embodiments of the intravascular stents as described herein will be described with reference to appended drawings.

First Embodiment

Figure 1:
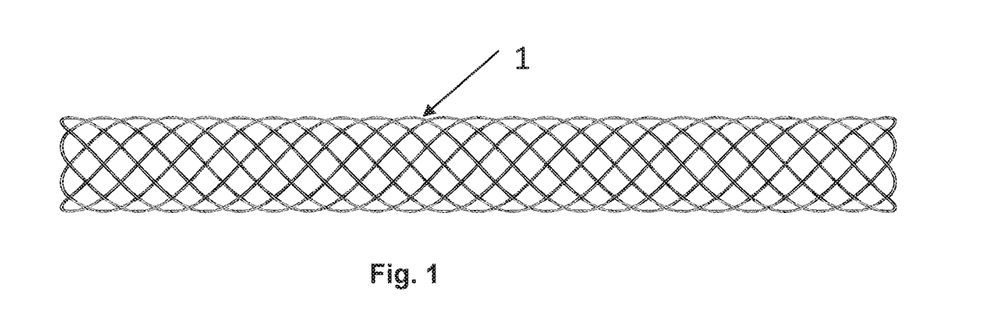
FIG. 1 is a schematic structural view of the intravascular stent according to one embodiment as described herein.

FIG. 1 is a schematic structural view of the intravascular stent according to one embodiment as described herein. FIG.

Figure 2A:
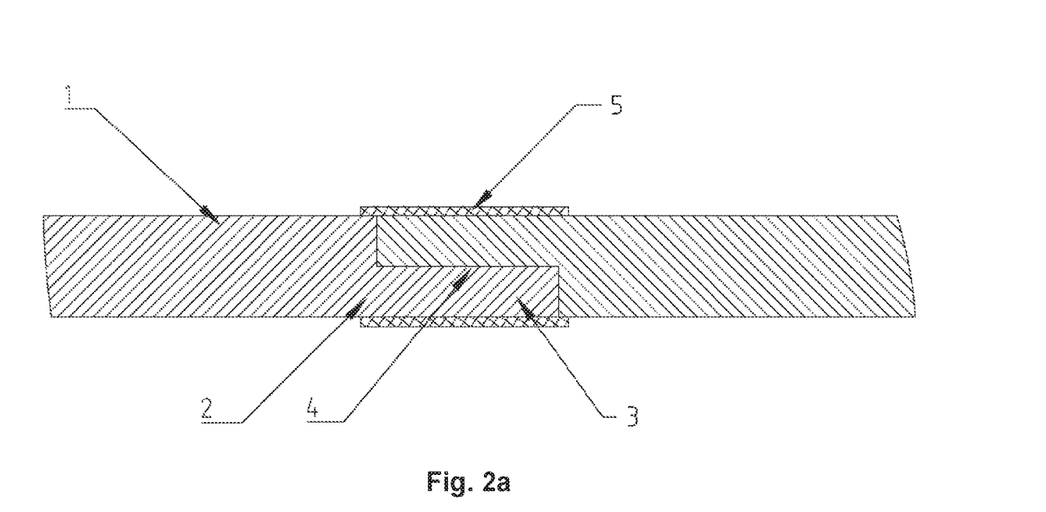
FIG. 2a is a schematic cross-sectional view of the joint portion of FIG. 1.
Figure 2B:
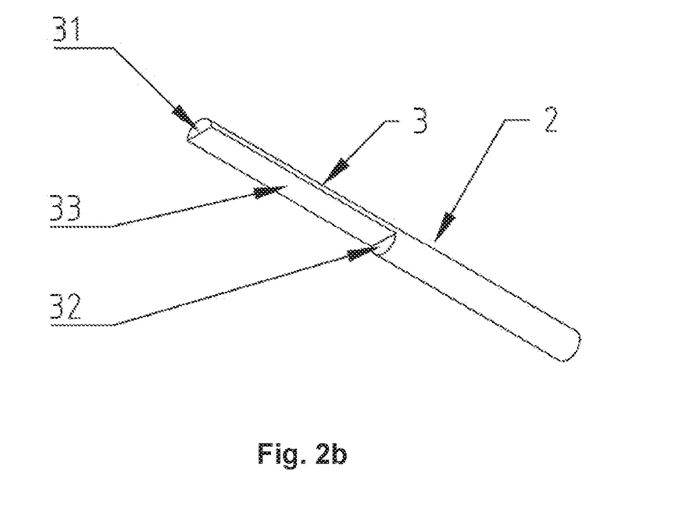
FIG. 2b is a perspective view of the free end of the woven wire.
Figure 2C:
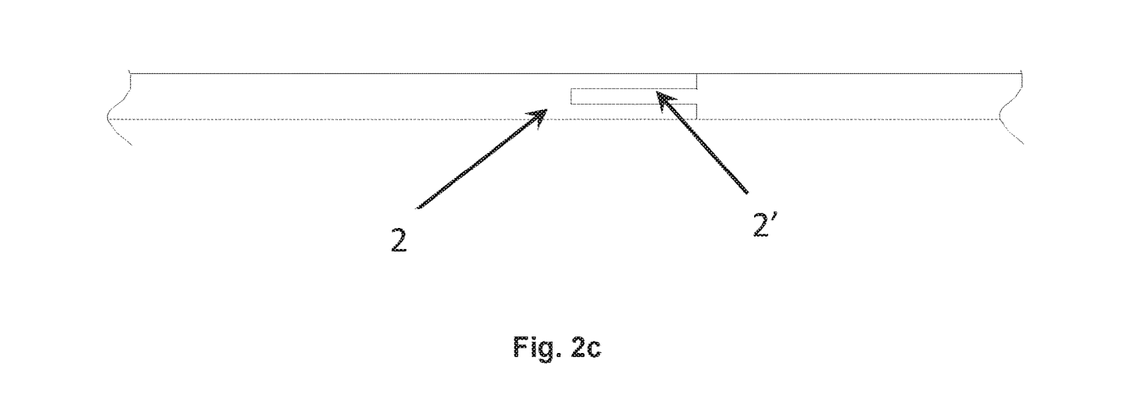
FIG. 2c is another schematic cross-sectional view of the joint portion of FIG. 1.
Figure 3:
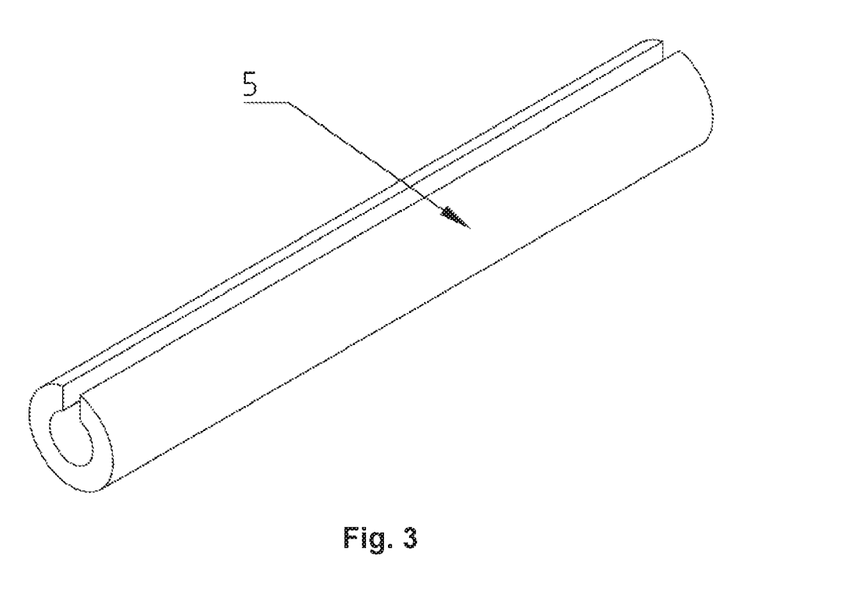
FIG. 3 is a perspective view of the coupling tube of FIG. 1.

2a is a schematic cross-sectional view of the joint portion of FIG. 1, FIG. 2b is a perspective view of the free end of the woven wire, and FIG. 2c is another schematic cross-sectional view of the joint portion of FIG. 1. FIG. 3 is a perspective view of the coupling tube of FIG. 1.

As shown in FIGS. 1 to 2c, the stent is woven by eight wires 1, and the woven stent is in a tubular structure. Each wire 1 has two free ends which are joints for the wire. There are sixteen free ends for eight wires. In other words, the at least one wire which forms the stent has an even number of free ends. The free ends 2 of the eight wires 1 are aligned and jointed together with each other, and thus a joint portion is formed. Alternatively, the number of wires is not limited to 8, which may be 1, 2, 3, 4, 5, 6, 7, 9, 10, 11, 12 or more.

As shown in FIG. 2a, each free end 2 of the wire 1 has a cutting portion 3. The cutting portions 3 of the two free ends 2 that are aligned and jointed together are seamlessly connected with each other to form a joint portion 4 with a diameter identical to that of the wire 1. The joint portion 4 is covered by a coupling tube 5, and the inner wall of the coupling tube 5 is seamlessly connected to the outer wall of the joint portion 4. As shown in FIG. 2b, the wire 1 has a circular cross section and the cutting portion of the free end 2 is a semi-cylinder. Such configuration is convenient for cutting and jointing, and the two semi-cylinders can be jointed together into a cylinder. The cutting portion 3 includes a top end surface 31, a bottom end surface 32 and a side wall surface 33. The two side wall surfaces 33 of the two cutting portion that are aligned and jointed together are abutted against each other, and the two top end surfaces 31 are respectively abutted against the corresponding bottom end surfaces 32. The cutting portions are seamlessly connected with each other. Moreover, the two side wall surfaces have a matching concave-convex structure, or other structure which could make the two side wall surfaces more securely connect with each other, to improve the stability of connection of the free ends.

In an alternative embodiment, the joint portion is not covered by a coupling tube.

As shown in FIG. 2c, the cutting portion of the free end 2 also has a concave-convex structure. For example, the cutting portion of the free end 2 has a groove, and the corresponding cutting portion of the corresponding free end 2' has a corresponding projection. Both the groove and the projection are convenient for cutting and jointing. The groove of the free end 2 and the projection of the free end 2' can be well snapped and jointed together. The diameter and the shape of the joint portion that are formed by jointing two free ends are identical to those of the wire. Such a concave-convex structure can make the two free ends more securely connect with each other and improve the stability of connection of the free ends. As such, the coupling tube can be omitted.

Alternatively, the cutting portions may be other shape, which could make the cutting portions of the two free ends that are aligned and jointed together match each other and the two free ends can be engaged into a joint portion with a diameter identical to that of the wire.

In this embodiment, the cutting portions of the two free ends that are aligned and jointed together are fixed by laser welding, which is convenient with fastness and stability.

As shown in FIG. 3, the coupling tube may be a C-Clip tube with an axial opening which can be closed by clamping. Such opening is also convenient for laser welding. The inner wall of the coupling tube and the outer wall of the joint portion may be fixed by laser welding or clamping deformation, preferably by laser welding. Alternatively, the connecting tube may also be sleeves with other structures; or other structures that can be unfolded to wrap the joint portion and then be clamped to close the opening.

As shown in FIG. 1, the stent is woven by crossing-overlapping forward braiding wire(s) 1 and backward braiding wire(s) 1. The forward braiding wire(s) and backward braiding wire(s) adjacent to each other peripherally form diamond grid units. The switching section of the forward braiding wire(s) and backward braiding wire(s) are the rounded corners of the two ends of the stent. Specifically, the wires are forward braided from the front to the back and then backward braided from the back to the front. The cross-overlapping means that the backward braiding wire is over the forward braiding wire at one contact and the backward braiding wire is under the forward braiding wire at the next contact. The obtuse angles ∅ of the diamond grid units range from 91 to 179 degrees, from 100 to 160 degrees, from 110 to 150 degrees, from 115 to 140 degrees, or from 120 to 135 degrees. The shape of the cross section of the wires is selected from the group consisting of round, ellipse, trapezoid, diamond, or rectangle. The wire is made from at least one of nickel-titanium alloy, platinum, gold, tantalum, etc., for example, 304 stainless steel, 316L stainless steel, L605 cobalt-chromium alloy, and MP35N alloy.

Second Embodiment

Figure 4A:
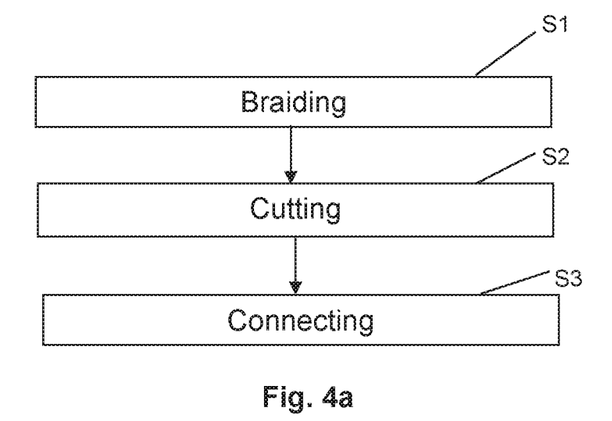
FIG. 4 is a schematic view of a method for manufacturing an intravascular stent according to one embodiment as described herein.
Figure 4B:
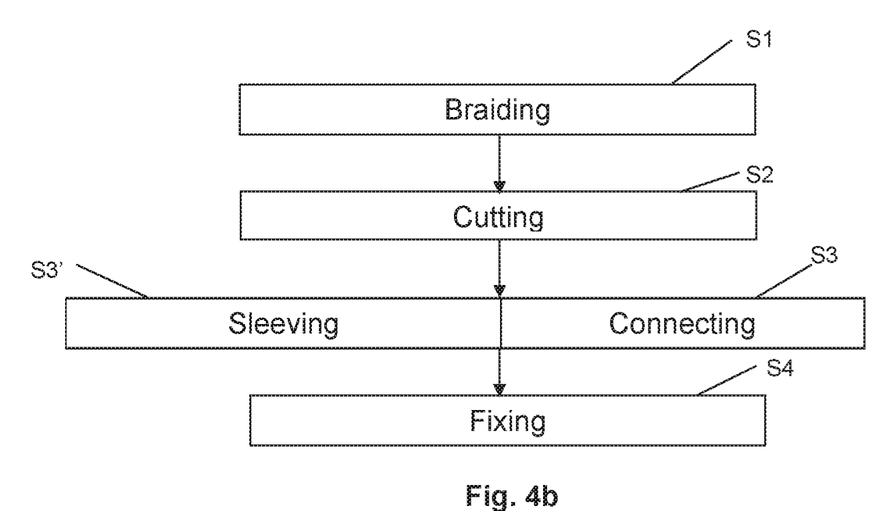

Embodiments as described herein also provide a method for manufacturing an intravascular stent. FIGS. 4a and 4b are schematic views of a method for manufacturing an intravascular stent according to one embodiment as described herein.

As shown in FIG. 4a, the method for manufacturing an intravascular stent comprises:

S1, Braiding: forward braiding and backward braiding at least one wire in a crossing-overlapping mode with exposed free ends of the wire. Specifically, the at least one wire is forward braided from the front to the back, when the forward braiding wire arrives tail, the wire is backward braided from the back to the front. The forward braiding wire and backward braiding wire are in a crossing-overlapping mode, which peripherally form diamond grid units. The stent is in a tubular structure.

S2. Cutting: cutting the exposed free ends to form cutting portions. For example, all the cutting portions of the free ends are semi-cylinders with same specifications, and two semi-cylinders can be jointed together into a cylinder. Alternatively, the free ends can be cut into other shapes which could match each other, for example, one free end has a projection and the other free end has a corresponding groove, and so on.

S3. Connecting: connecting the cutting portions of the two free ends that are aligned and jointed together. The connected free ends can be fixed by laser welding and so on.

As shown in FIG. 4b, the manufacturing method may further comprise:

S3'. Sleeving: connecting the two free ends that are aligned and jointed together with the coupling tube. For example, one of the two free ends that are aligned and jointed together is inserted into the coupling tube and the other end is inserted into the coupling tube from the opposite direction and the cutting portions of the two free ends are connected. This step may also be adjusted to, for example, insert one of the two free ends that are aligned and jointed together through the coupling tube, then joint the two free ends to connect the cutting portions of the two free ends, next move the coupling tube to cover the joint portion. This step may also be adjusted to, for example, joint the two free ends to connect the cutting portions of the two free ends, then cover the coupling tube on the joint portion, next clamp the coupling tube or fix the coupling tube by other means.

S4. Fixing: fixing the coupling tube and the free ends. For example, the fixing step may include performing laser welding to seamlessly weld the coupling tube and the free ends as a whole; or clamping the coupling tube to make the coupling tube and the free ends be seamlessly fixed as a whole; or clamping the coupling tube and then performing laser welding to seamlessly weld the coupling tube and the free ends as a whole.

For such intravascular stent, the joint portion of the free ends of the wire thereof is seamlessly connected with the coupling tube, and thus the radial force and axial force of the free ends is uniformly distributed. Meanwhile, the stent is convenient for laser welding to stabilize the connection of free ends; moreover, the intravascular stent has great flexibility and perfect appearance.

Third Embodiment

Figure 5:
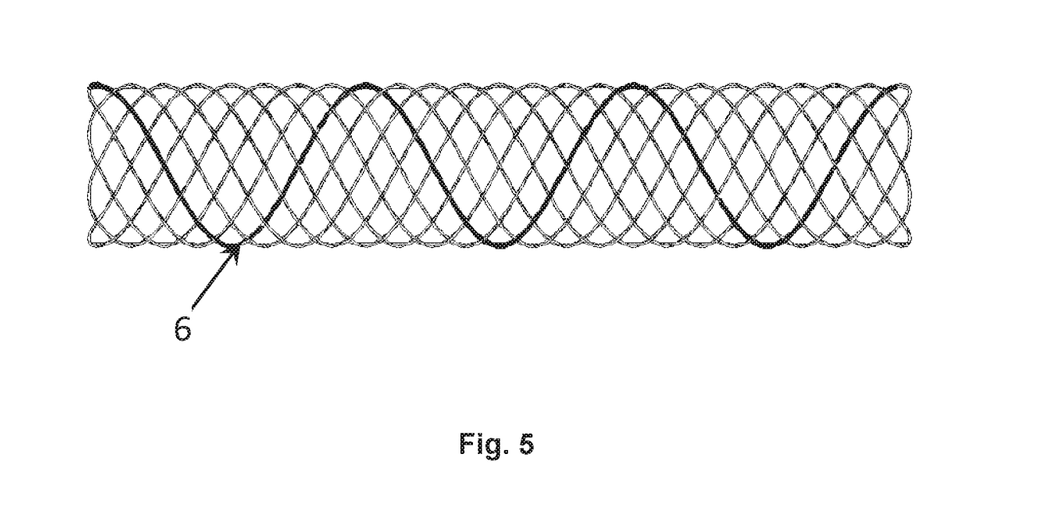
FIG. 5 is a schematic structural view of the intravascular stent according to another embodiment as described herein.
Figure 6:
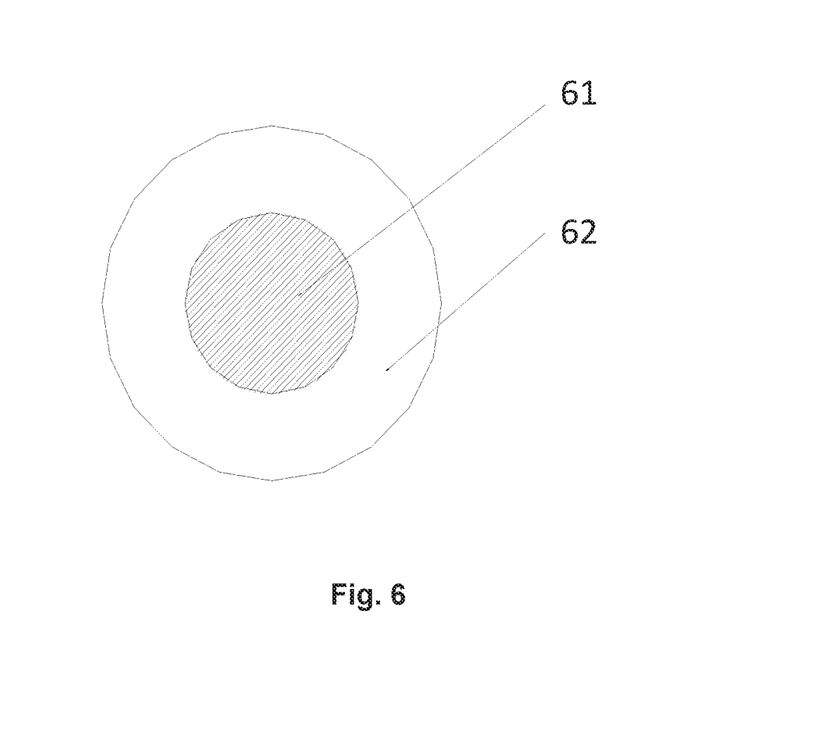
FIG. 6 is a schematic cross-sectional view of the radiopaque wire of FIG. 5.
Figure 7:
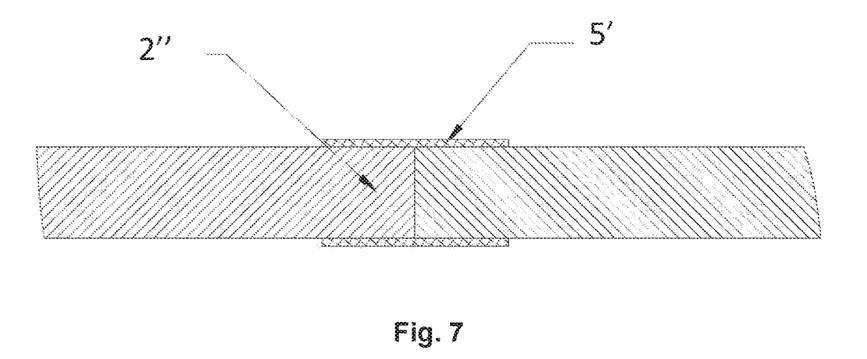
FIG. 7 is a schematic cross-sectional view of the coupling tube and the free end of FIG. 5.

FIG. 5 is a schematic structural view of the intravascular stent according to another embodiment as described herein. FIG. 6 is a schematic cross-sectional view of the radiopaque wire of FIG. 5. FIG. 7 is a schematic cross-sectional view of the coupling tube and the free end of FIG. 5.

As shown in FIG. 5, the stent is woven by at least two wires 1 (for example eight wires). The stent woven by wires 1 is in a tubular structure. The at least two wires 1 have an even number of free ends. The free ends of the at least two wires 1 are aligned and jointed together with each other.

For example, the stent is woven by eight wires 1, in which any one of the wires is a radiopaque wire 6. One radiopaque wire is able to meet the needs of radiopaque operation and can reduce the cost of the product. Alternatively, any one or two or more of the wires (for example, 3, 4, 5, 6, 7 or more or all of the wires) is/are radiopaque wire(s). Alternatively, the stent is formed by other number of wires (for example, 2, 3, 4, 5, 6, 7, 9, 10, 11, 12 or more wires or other number of wires).

As shown in FIG. 6, the radiopaque wire 6 includes a core 61 formed by radiopaque material and an outer peripheral portion 62 wrapped around the core 61. The cross-sectional area of the core 61 comprised of 30% to 50% of the cross-sectional area of the radiopaque wire, or 35% to 45%, or other numerical ranges. The radiopaque material is selected from any of the following materials: platinum, platinum iridium alloy, tantalum, gold and the like. The outer peripheral portion is made of nickel-titanium alloy. Alternatively, the radiopaque wire may be other configuration, for example, the radiopaque wire may be made by materials that are obtained by mixing radiopaque material and nickel-titanium alloy. As such, the radiopaque material is 10%-90%, or 20%-80%, or 30%-70%, or 40%-60%, or other numerical ranges of the nickel-titanium by mass.

The stent of this embodiment may also have the structural features of the stent as described in the first embodiment. For example, the stent is woven by forward braiding and backward braiding wire(s) 1 in a crossing-overlapping mode. The forward braiding wire(s) and backward braiding wire(s) peripherally adjacent to each other form diamond grid units. The switching section of the forward braiding wire(s) and backward braiding wire(s) are the round corners at the two ends of the stent. The obtuse angles ∅ of the diamond grid units range from 91 to 179 degrees, from 100 to 160 degrees, from 110 to 150 degrees, from 115 to 140 degrees, or from 120 to 135 degrees. For example, the shape of the cross section of the wires is round, ellipse, trapezoid, diamond, or rectangle.

The free ends of the wire(s) or radiopaque wire(s) of the stent of this embodiment may also have the cutting portion as described in the first embodiment to improve the stability of connection of the free ends.

The tubular structure of the stent has two ends, one of which is a narrow end and the other is a wide end. The diameter of the narrow end is smaller than the diameter of the wide end. The stent is in a tapered cylinder structure with the diameter gradually increased from the narrow end to the wide end. When using such intravascular stent, the stent can be introduced in accordance with the width of the blood vessel, so that the wide end of the stent corresponds to the wide part of the blood vessel and the narrow end of the stent corresponds to the narrow part of the blood vessel. Thus the stent matches the inner wall of the blood vessel. Such stent provides uniform pressure to the inner wall of blood vessels and will not cause topical compression or topical insufficient support.

Fourth Embodiment

This embodiment is similar to the third embodiment except that the radiopaque configuration. In this embodiment, there are many joints in the stent since the stent is woven by the wires. As shown in FIG. 7, the wires may have an even number of free ends 2", and the free ends are aligned and jointed together with each other and covered by coupling tubes 5'. At least part of the coupling tubes 5' are radiopaque coupling tube(s). Both the coupling tube(s) and the wires have radiopaque feature.

The radiopaque coupling tube(s) can be distributed evenly along the axial direction of the stent. For example, in the case that the stent is woven by eight wires, four of the eight coupling tubes are radiopaque and distributed evenly along the axial length of the stent. The number of the radiopaque coupling tubes is not limited and may also be 1, 2, 3, 4, 5, 6, 7, otherwise all of the coupling tubes are radiopaque. The radiopaque coupling tube(s) may also be set at one or both ends of the stent to meet the needs of radiopaque operation. The number of wires may also be other numbers (e.g., 2, 3, 4, 5, 6, 7, 9, 10, 11, 12 or more or other numbers).

Alternatively, at least part of the coupling tubes may be radiopaque (for example, 1, 2, 3, 4, 5, 6, 7 or more or all of the coupling tubes are radiopaque coupling tube(s)), or at least one of the wires is a radiopaque wire (for example, 2, 3, 4, 5, 6, 7 or more or all of the wires are radiopaque), to meet the needs of radiopaque operation.

In this embodiment, both the coupling tubes 5' and the radiopaque coupling tube(s) may be C-Clip tubes. Alternatively, the coupling tubes may also have other configuration, such as sleeves.

The radiopaque coupling tube(s) may be made of radiopaque material, which may be selected from any of the following materials: platinum, platinum iridium alloy, tantalum, gold, and the like. The cross-sectional shape of the radiopaque coupling tube(s) may be circular, hexagonal or C-shaped.

Fifth Embodiment

Figure 8:
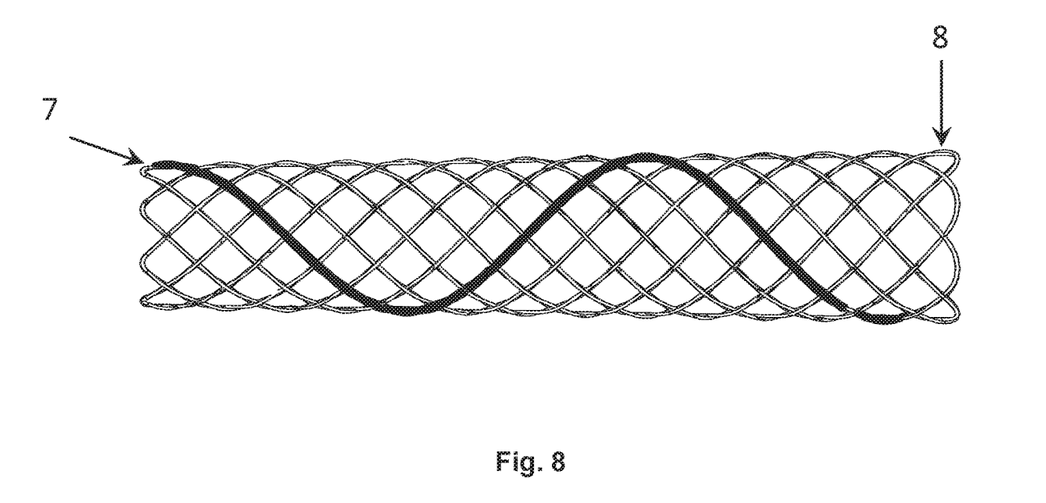
FIG. 8 is a schematic structural view of the intravascular stent according to yet another embodiment as described herein.

FIG. 8 is a schematic structural view of the intravascular stent according to another embodiment as described herein.

This embodiment is similar to the third embodiment except that the stent is conical instead of including a radiopaque configuration.

As shown in FIG. 8, in this embodiment, the tubular structure of the stent has two ends, one of which is a narrow end 7 and the other is a wide end 8. The diameter of the narrow end 7 is smaller than the diameter of the wide end 8. The stent is in a tapered cylinder structure with the diameter gradually increased from the narrow end to the wide end. For example, the length of the stent is larger than 100 mm, the diameter ratio of the wide end 8 and the narrow end 7 ranges from 1.1 to 1.5, or from 1.2 to 1.4, or other numerical ranges.

When using such intravascular stent, the stent can be introduced in accordance with the width of the blood vessel, so that the wide end of the stent corresponds to the wide part of the blood vessel and the narrow end of the stent corresponds to the narrow part of the blood vessel. Thus the stent matches the inner wall of the blood vessel. Such a stent provides uniform pressure to the inner wall of blood vessels and will not cause topical compression or topical insufficient support.

The stent of this embodiment may also be provided with a radiopaque configuration as described in the third embodiment or the fourth embodiment, for example, at least one of the wires may be radiopaque, and/or at least part of the coupling tubes is radiopaque, or the like, to meet the need for radiopaque operation.

The stent of this embodiment may also include the cutting portion as described in the first embodiment to improve the stability of connection of the free ends.

The stent of this embodiment may also have the structural features of the stent as described in the first embodiment, so that the stent is excellent in softness and appearance.

It should be noted that although the aspects of the above-described stents and manufacturing methods are described in terms of specific structural arrangements and specific sequences, the detailed description is merely a specific illustration of the embodiment of the present invention. The present invention is not to be limited to the detailed description, and the claimed subject matter is not limited to the described construction. It will be understood by those skilled in the art that various modifications may be made to the invention without departing from the spirit of the invention and equivalents may be substituted. Accordingly, the claimed subject matter is not to be limited to the specific embodiments disclosed above, but may include all technical solutions falling within the scope of the claims and the equivalent technical solutions therewith. Furthermore, in the claims, all terms should be understood in the broadest sense unless otherwise indicated.

What we claimed is:

1. An intravascular stent, woven by one to twelve wires and is in a tubular structure, wherein, at least one of the one to twelve wires is a radiopaque wire, wherein, the one to twelve wires have an even number of ends, and the ends of the one to twelve wires are aligned and jointed together with each other, and wherein, the ends of the one to twelve wires all have cutting portions, and the cutting portions of two ends that are aligned and jointed together match each other to form a joint portion with a diameter identical to that of the wire,
wherein the cutting portion of the ends is a semi-cylinder, the cutting portion includes a top end surface, a bottom end surface, and a side wall surface, the two side wall surfaces of the two cutting portions that are aligned and jointed together are abutted against each other, and the two top end surfaces are respectively abutted against the corresponding bottom end surfaces, and the two side wall surfaces have a matching concave-convex structure.

2. The intravascular stent according to claim 1, wherein, the joint portion is covered by a coupling tube, and the inner wall of the coupling tube is seamlessly connected to the outer wall of the joint portion.

3. The intravascular stent according to claim 2, wherein, the coupling tube is a C-Clip tube.

4. The intravascular stent according to claim 1, wherein, the cutting portions of the two ends that are aligned and jointed together are fixed by laser welding.

5. The intravascular stent according to claim 2, wherein, the coupling tube and the joint portion are fixed by laser welding or clamping deformation.

6. The intravascular stent according to claim 1, wherein, the intravascular stent is woven by forward braiding and backward braiding the wire in a crossing-overlapping mode, the forward braiding wire and backward braiding wire peripherally adjacent to each other form diamond grid units, a switching section of the forward braiding wire and backward braiding wire are rounded corners at the two ends of the stent.

7. The intravascular stent according to claim 6, wherein, obtuse angles are formed in the diamond grid units that range from 91 to 179 degrees, from 100 to 160 degrees, from 110 to 150 degrees, from 115 to 140 degrees, or from 120 to 135 degrees.

8. The intravascular stent according to claim 6, wherein, the shape of the cross section of the wires is round, ellipse, trapezoid, diamond, or rectangle.

9. The intravascular stent according to claim 6, wherein, the one to twelve wires are made from any of the following materials: nickel-titanium alloy, 304 stainless steel, 316L stainless steel, L605 cobalt-chromium alloy, or MP35N alloy.

10. The intravascular stent according to claim 1, wherein, the radiopaque wire includes a core formed by radiopaque material and an outer peripheral portion wrapped around the core.

11. The intravascular stent according to claim 10, wherein, the cross-sectional area of the core comprises of 30%-50% of the cross-sectional area of the wire.

12. The intravascular stent according to claim 10, wherein, the outer peripheral portion is made of nickel-titanium alloy.

13. The intravascular stent according to claim 1, wherein, the radiopaque wire is made by mixing radiopaque material and nickel-titanium alloy, and wherein the radiopaque wire has a mass ratio of radiopaque material to nickel-titanium of 10-90%.

14. The intravascular stent according to claim 10, wherein, the radiopaque material is selected from a group consisting of: platinum, platinum iridium alloy, tantalum, and gold.

15. The intravascular stent according to claim 1, wherein, there are a plurality of joint portions covered by a plurality of coupling tubes, wherein at least one of the plurality of coupling tubes is radiopaque.

16. The intravascular stent according to claim 15, wherein, the radiopaque coupling tubes are set at one or both ends of the stent or are distributed evenly along the axial direction of the stent.

17. The intravascular stent according to claim 1, wherein, the tubular structure of the stent has two ends, one of which is a narrow end and the other is a wide end, the diameter of the narrow end is smaller than the diameter of the wide end, the stent is in a tapered cylinder structure with the diameter gradually increased from the narrow end to the wide end.

18. The intravascular stent according to claim 15, wherein, the cross-sectional shape of the radiopaque coupling tube is circular, hexagonal or C-shaped.

19. An intravascular stent, woven by one to twelve wires and is in a tubular structure, wherein, at least one of the one to twelve wires is a radiopaque wire, wherein, the one to twelve wires have an even number of ends, and the ends of the one to twelve wires are aligned and jointed together with each other, and wherein, the ends of the one to twelve wires all have cutting portions, and the cutting portions of two ends that are aligned and jointed together match each other to form a joint portion with a diameter identical to that of the wire, wherein, the cutting portion of the free end has a concave-convex structure.

* * * * *